US011681726B2

(12) United States Patent
Ghalwash et al.

(10) Patent No.: US 11,681,726 B2
(45) Date of Patent: Jun. 20, 2023

(54) SYSTEM FOR GENERATING SPECIALIZED PHENOTYPICAL EMBEDDING

(71) Applicant: International Business Machines Corporation, Armonk, NY (US)

(72) Inventors: Mohamed Ghalwash, Westchester, NY (US); Zijun Yao, Ridgewood, NJ (US); Prithwish Chakraborty, New York, NY (US); James V Codella, Danbury, CT (US); Daby Mousse Sow, Croton on Hudson, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 98 days.

(21) Appl. No.: 17/110,954

(22) Filed: Dec. 3, 2020

(65) Prior Publication Data
US 2022/0179880 A1 Jun. 9, 2022

(51) Int. Cl.
*G06F 17/00* (2019.01)
*G06F 16/28* (2019.01)
*G06N 20/00* (2019.01)
*G16H 10/60* (2018.01)

(52) U.S. Cl.
CPC .......... *G06F 16/284* (2019.01); *G06N 20/00* (2019.01); *G16H 10/60* (2018.01)

(58) Field of Classification Search
CPC ....... G06F 16/284; G06N 20/00; G16H 10/60
See application file for complete search history.

(56) References Cited

U.S. PATENT DOCUMENTS

| 9,672,814 | B2 | 6/2017 | Cao et al. |
| 10,755,810 | B2 * | 8/2020 | Buckler ................. G16H 30/40 |
| 2017/0337268 | A1 | 11/2017 | Ait-Mokhtar et al. |
| 2019/0057774 | A1 | 2/2019 | Velez et al. |
| 2020/0118682 | A1 * | 4/2020 | Villazón-Terrazas et al. .............. G16H 50/20 |

OTHER PUBLICATIONS

Choi et al., "MiME: Multilevel Medical Embedding of Electronic Health Records for Predictive Healthcare." 32nd Conference on Neural Information Processing Systems (NeurIPS 2018), Montreal, Canada. Advances in Neural Information Processing Systems, pp. 4547-4557, 2018.

(Continued)

*Primary Examiner* — Greta L Robinson
(74) *Attorney, Agent, or Firm* — Amin, Turocy & Watson, LLP

(57) ABSTRACT

Systems and methods that use multi-tasking and transfer learning with sparse gating mechanisms and domain knowledge to generate pheno-embeddings in a scalable manner that can improve the relevance of the patient embeddings from Electronic Health Records. A system, comprises at least one processor that executes the following computer executable components stored in memory: a structural pheno-embedding model that employs a hierarchical knowledge graph; a data augmentation component that expands on a sparse data set associated with the knowledge graph; and an embedding component that generates a specialized embedding for phenotypes using the structural pheno-embedding model and the augmented data set for a selected cohort.

21 Claims, 9 Drawing Sheets

(56) References Cited

OTHER PUBLICATIONS

Choi et al. "GRAM: graph-based attention model for healthcare representation learning." In Proceedings of the 23rd ACM SIGKDD International Conference on Knowledge Discovery and Data Mining (KDD '17). ACM, pp. 787-795, 2017.
Dubois et al., "Effective Representations of Clinical Notes." (Submitted on May 19, 2017 (v1), last revised Aug. 16, 2018 (this version, v3)), https://arxiv.org/abs/1705.07025.
Choi et al. "Learning Low-Dimensional Representations of Medical Concepts" AMI Joint Summits on Translational Science Proceedings. AMI Joint Summits on Translational Science vol. 2016 41-50. Jul. 20, 2016.
Khattak et al., "A survey of word embeddings for clinical text," Preprint submitted to Journal of Biomedical Informatics. (Uploaded by F. Khattak on Aug. 26, 2019), https://www.researchgate.net/publication/332543716.
Choi et al., "Multi-layer representation learning for medical concepts." In Proceedings of the 22nd ACM SIGKDD International Conference on Knowledge Discovery and Data Mining, KDD '16, pp. 1495-1504, 2016.

* cited by examiner

SYSTEM FOR GENERATING SPECIALIZED PHENOTYPICAL EMBEDDING

TECHNICAL FIELD

The subject disclosure relates to using multi-task and transfers learning with sparse gating mechanisms and domain knowledge to generate pheno-embeddings in a scalable manner to improve the relevance of the patient embeddings from Electronic Health Records.

BACKGROUND

Discovering efficient representations of high dimensional concepts has been a challenge in a variety of medical applications. By using various types of neural networks, high-dimensional data can be transformed into continuous real-valued concepts that can efficiently capture relationships from the data. These types of data representations have shown improvement in the performance of various complex tasks across domains spanning from image processing, language modeling, word embedding, and multi-modal learning of images and text. Efficient representations for medical concepts are significant, if not essential, element in healthcare applications. Many medical concepts contain rich latent relationships that cannot be represented by a simple data representation. In computational health, many academics have developed methods to generate patient embeddings from Electronic Health Records (EHR) data. These algorithms produce vector representation of patient history and provide a temporal point-wise assessment of the state of the patient that can be utilized for Artificial Intelligence modeling. However, such methods do not utilize medical knowledge expressed via phenotypical attributes of patients that can improve the relevance of the embeddings. Moreover, in the EHR analysis, constructed cohorts are often too small in size for common deep learning methods, including such domain information and can increase the robustness, and applicability of patient representations.

SUMMARY

The following presents a summary to provide a basic understanding of one or more embodiments of the invention. This summary is not intended to identify key or critical elements, delineate scope of particular embodiments or scope of claims. Its sole purpose is to present concepts in a simplified form as a prelude to the more detailed description that is presented later. In one or more embodiments described herein, systems, computer-implemented methods, apparatus and/or computer program products facilitate generation using multi-task and transfer learning with sparse gating mechanisms and domain knowledge to generate pheno-embeddings in a scalable manner that can improve the relevance of the patient embeddings from Electronic Health Records.

In accordance with an embodiment, a system comprises: at least one processor that executes the following computer executable components stored in memory, wherein the computer executable components comprise: a structural pheno-embedding model that employs a hierarchical knowledge graph; a data augmentation component that expands on a sparse data set associated with the hierarchical knowledge graph; and an embedding component that generates a specialized embedding for phenotypes using the structural pheno-embedding model and the augmented data set for a selected cohort.

In an optional aspect, a graph generation component populates the hierarchical knowledge graph with medical data.

In another aspect, a model generation component generates the structural pheno-embedding model using the hierarchical knowledge graph.

In yet another aspect, a training component trains the structural pheno-embedding model using a set of vendor data.

In an optional aspect, a training component trains the structural pheno-embedding model using a set of client data.

In accordance with an embodiment, a computer-implemented method comprises: using a structural pheno-embedding model that employs a hierarchical knowledge graph; expanding on a sparse data set associated with the hierarchical knowledge graph; and generating a specialized embedding for phenotypes using the structural pheno-embedding model and the augmented data set for a selected cohort.

In an optional aspect, the method further comprises populating, using a graph generation component, the hierarchical knowledge graph with medical data In an optional aspect, the method further comprises generating, using a model generation component, the structural pheno-embedding model using the hierarchical knowledge graph.

In another aspect, the method further comprises training, using a training component, the structural pheno-embedding model using a set of vendor data.

In an additional aspect, the method further comprises using a training component, the structural pheno-embedding model using a set of client data.

In an optional aspect, the method further comprises augmenting, using an augmentation component, a filtered graph of medical concepts.

In yet another aspect, the method further comprises minimizing a hierarchical loss function that comprises reconstruction loss and task-specific loss.

DETAILED DESCRIPTION

Figure 1:
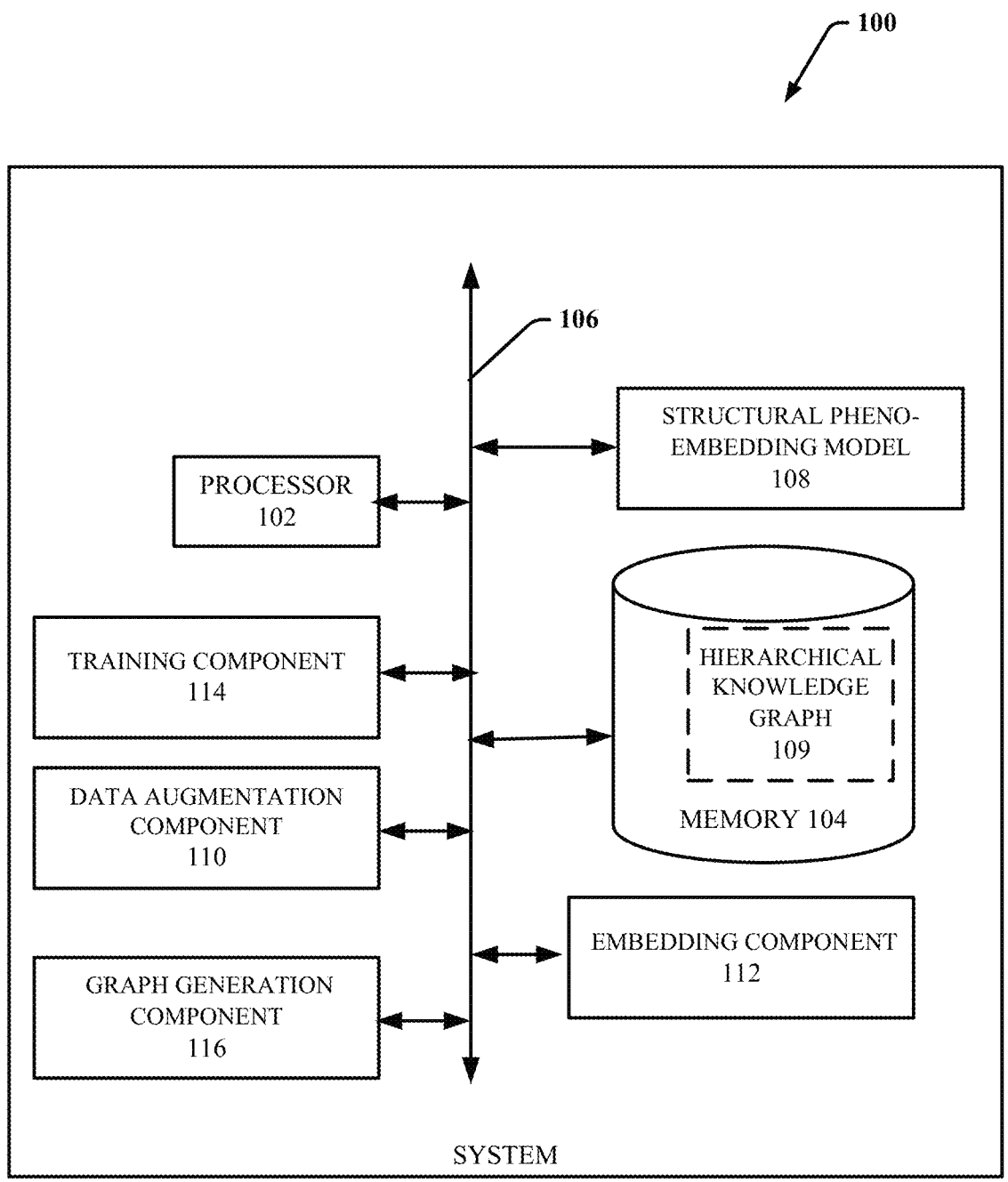
FIG. 1 illustrates a block diagram of an example system implementation that implements a system to generate specialized phenotypical embedding.

The following detailed description is merely illustrative and is not intended to limit embodiments and/or application or uses of embodiments. Furthermore, there is no intention to be bound by any expressed or implied information presented in the preceding Summary section, or in the Detailed Description section. One or more embodiments are now described with reference to the drawings, wherein like reference numerals are used to refer to like elements throughout. In the following description, for purposes of explanation, numerous specific details are set forth in order to provide a more thorough understanding of the one or more embodiments. It is evident; however, in various cases, that the one or more embodiments can be practiced without these specific details.

The subject disclosure relates generally to systems and methods that generate specialized embedding using a hierarchical knowledge graph for the selected cohort. This method expands to a data representation model that is fully trained on vendor data. The model can be used by the client to generate embedding for the client's data. The data representation model that is initially trained on vendor data can further be tuned on client data for existing nodes and new nodes. Also, the data representation model that is not trained on vendor data can be fully trained on the client's data.

In today's digital world, the use of artificial intelligence has increased exponentially. Artificial intelligence (AI) simulates human intelligence processes by machines such as computer systems. These processes include learning wherein the information is acquired, reasoning wherein the information is used to reach approximate conclusions, and lastly, self-correction. AI is progressing rapidly from SIRI to self-driving cars. AI can be categorized as weak AI (narrow AI) or strong AI (general AI). Weak AI is designed to perform a narrow task such as facial recognition, driving a car, performing surgery, and many virtual technical advancements such as Apple's SIRI. Strong AI is designed to work on unfamiliar tasks where with human cognitive abilities, it can find a solution without human intervention. Thus, AI makes it possible for machines to learn from experience, adjust to new inputs and perform human-like tasks. In comparison with cognitive computing, artificial intelligence discovers patterns in big data to learn and reveal hidden information or deliver solutions to complex problems. Artificial intelligence is used in many applications such as automation, speech recognition, machine learning, robotics, and machine vision. AI is the main subject in today's technological advancement because it automates repetitive learning and discovery through data analysis and adds intelligence, adapts through progressive learning algorithms, achieves accuracy and produces accurate results. AI has made its way in major application areas such as banking, healthcare, retail, education, and manufacturing. In particular, Artificial Intelligence brings a paradigm shift to healthcare by increasing the availability of healthcare data, and the rapid progress of analytics techniques.

Artificial intelligence can provide various types of structured and unstructured healthcare data. Applications in healthcare provide personalized medicines and X-ray readings. Some popular AI techniques include machine learning methods for structured data, such as the classical support vector machine and neural network. Modern deep learning and natural language processing are other techniques used for unstructured data. Machine learning uses a statistical technique to fit models to data and learn by training the models with the data. It is the most common form used in Artificial Intelligence wherein predicting the treatment that is likely to succeed on a patient based on various patient attributes and treatment context. This is called supervised learning such that machine learning and precision medicine applications utilize a training dataset for which the outcome variable is known. Moreover, the neural network is one of the complex forms of machine learning. It is used to categorize applications by determining whether a patient can acquire a particular disease. It views the inputs, outputs, and weights the variables that associate inputs with the outputs, and analyze the problem further. The neural network model with many levels is also known as deep learning that predicts the outcome. One of the common applications of deep learning in healthcare is to recognize potential cancerous lesions in radiology images. Deep learning is also used for radionics to detect features in imaging data beyond what can be perceived by the human eye. Radionics and deep learning are commonly used in oncology-oriented image analysis. This combination provides greater accuracy during the diagnosis process.

In the healthcare industry, one of the major studies is focused on the utilization of Artificial Intelligence (AI) in generating patient embeddings from Electronic Health Records (EHR). Inspired by NLP embedding approaches, these algorithms produce vector representations of patient history and provide a temporal point-wise assessment of the state of the patient that can be used for Artificial Intelligence modeling. Patient data from large scale EHR are of increasing interest for clinical hypothesis generation and testing. These datasets may contain information regarding medical history of many patients and cover varied aspects such as diagnosis, medication and lab tests. However, these data can be noisy, sparse, and non-uniformly distributed such that the studies outcome can lead to modest number of useful patient records. These data sets are often insufficient to learn the underlying complex disease phenomena, especially with deep learning models. Thus, AI capabilities can unleash the full potential of data to improve patient's health and solve health care challenges. This evolution can enable health care organizations to empower physicians with accurate diagnostics and provide targeted prevention capabilities. It can also improve operational performance by optimizing resources and reduce number of hospital readmissions. However, such methods do not utilize medical knowledge expressed via phenotypical attributes of patients that can improve relevance of embeddings. Moreover, in EHR analysis, constructed cohorts are often too small in size for common deep learning methods; including such domain information can increase robustness and applicability of patient representations. Thus, embodiments herein propose a system built on a novel concept of pheno-embeddings that are specialized representations learned for different patient phenotypes addressing data limitation(s) and the lack of relevance of embeddings issues. To learn such phenotypical patient representations, embodiments propose a novel system using multi-task and transfer learning with sparse gating mechanisms and domain knowledge to generate pheno-embeddings in a scalable manner. The proposed methods facilitate deploying a framework for large scale EHR analysis, and the ability to generate reusable robust patient representations at phenotype levels.

FIG. 1 illustrates a block diagram of an example system 100 that can access data and process that data using variable computing components depicted in accordance with one or more embodiments described herein. The system 100 can facilitate a process of assessing and identifying large amounts of various forms of data, using machine learning, and training a neural network or other type of model. The system 100 can also generate predictive recommendations to an individual level with context in accordance with one or more embodiments described herein. Aspects of systems (e.g., system 100 and the like), apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform operations described herein. Repetitive description of like elements employed in one or more embodiments described herein is omitted for sake of brevity.

The system 100 can facilitate a process of assessing and identifying a large amount of various forms of data. The system 100 can also generate predictive recommendations to an individual level resulting in a context in accordance with one or more embodiments described herein. Aspects of systems (e.g., system 100 and the like), apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. Repetitive description of like elements employed in one or more embodiments described herein is omitted for sake of brevity.

System 100 can optionally include a server device, one or more networks and one or more devices (not shown). The system 100 can also include or otherwise be associated with at least one processor 102 that executes computer executable components stored in memory 104. The system 100 can further include a system bus 106 that can couple various components including, but not limited to, a structural pheno-embedding model 108 that employs a hierarchical knowledge graph 109, a data augmentation component 110 that expands on a sparse data set associated with the hierarchical knowledge graph, an embedding component 112 that generates a specialized embedding for phenotypes using the structural pheno-embedding model and the augmented data set for a selected cohort. A training component 114 trains the structural pheno-embedding model 108, a graph generation component populates the hierarchical knowledge graph with medical data, and a model generation component 118 can generate the structural pheno-embedding model 108 using the hierarchical knowledge graph.

In an implementation, the structural pheno-embedding model 108 employs the hierarchical knowledge graph 109, and the graph generation component populates the hierarchical knowledge graph with medical data. The model generation component 108 generates the structural pheno-embedding model using the hierarchical knowledge graph 109. The data augmentation component 110 expands on a sparse data set associated with the hierarchical knowledge graph. The embedding component 112 generates a specialized embedding for phenotypes using the structural pheno-embedding model 108 and the augmented data set for a selected cohort. The structural pheno-embedding model 108 can be trained using a set of vendor or client data.

This system 100 facilitates an ontology driven framework for multi-tasking learning. A novelty of the proposed approach and system 100 is to ground structure of the multi-task framework on phenotypical medical concept relations between patients from different cohorts. This allows to learn outcome of different phenotypes from borrowing representation expressiveness from patients with similar phenotypes. Such sharing framework allows the model 108 to generate predictions for phenotypical cohorts even in phenotypes with few patient observation records. Moreover, this allows to decouple outcome learning from representation learning of similar diseases wherein the model 108 learns from patients with related diseases with different outcome. For example, mortality prediction for diabetic patients and readmission prediction can be learnt for patients with hypertension by sharing information between diabetes and hypertension. Despite a large number of patients in Electronic Health Records (EHR), a subset of usable data for modeling outcomes of specific phenotypes are often imbalanced and of modest size. This can be attributed to the uneven coverage of medical concepts in EHR. Thus, embodiments propose an approach to model different phenotypical cohorts and outcomes using domain knowledge in the form of medical concept ontological graphs. Moreover, these embodiments propose a hierarchical deep learning architecture with gating mechanisms to specialize outcome models for each phenotype using ontological relationship. This enables common representations to be shared across related phenotypes, and to improve learning performance.

System 100 can be any suitable computing device or set of computing devices that can be communicatively coupled to devices, non-limiting examples of which can include, but are not limited to, a server computer, a computer, a mobile computer, a mainframe computer, an automated testing system, a network storage device, a communication device, a web server device, a network switching device, a network routing device, a gateway device, a network hub device, a network bridge device, a control system, or any other suitable computing device. A device can be any device that can communicate information with the systems 100 and/or any other suitable device that can employ information provided by system 100. It is to be appreciated that systems 100, components, models or devices can be equipped with communication components (not shown) that enable communication between the system, components, models, devices, etc. over one or more networks.

The various components of systems 100 can be connected either directly or via one or more networks. Such networks can include wired and wireless networks, including, but not limited to, a cellular network, a wide area network (WAN) (e.g., the Internet), or a local area network (LAN), non-limiting examples of which include cellular, WAN, wireless fidelity (Wi-Fi), Wi-Max, WLAN, radio communication, microwave communication, satellite communication, optical communication, sonic communication, or any other suitable communication technology. Moreover, the aforementioned systems and/or devices have been described with respect to interaction between several components. It may be appreciated that such systems and components can include these components or sub-components specified therein, some of the specified components or sub-components, and/or additional components. Sub-components may also be implemented as components communicatively coupled to other components rather than included within parent components. Further yet, one or more components and/or sub-components can be combined into a single component providing aggregate functionality. The components can also interact with one or more other components not specifically described herein for the sake of brevity, but known by those of skill in the art.

The subject computer processing systems, methods apparatuses and/or computer program products can be employed to solve new problems that arise through advancements in technology, computer networks, the Internet and the like.

Electronic Health Record (EHR) is a digital record of a patient's data. It contains patient's medical and treatment history. It is a real-time record-keeping system that makes information available instantly and securely to authorized users. EHR has patient data set(s) with a list of features such as diagnosis codes, lab test results, vital signs, and many more. One of the many advantages of EHR is that health information can be created and managed by authorized users in a digital format and can be shared with other providers across health care organizations for further analysis. A Vendor owns and sells EHR data to clients based on criteria the client defines. Many clients are interested in data of patients with a specific type of disease such as Type 2 Diabetes. A vendor checks a data set and obtains Type 2 Diabetes patient's records and sells this data to a client. Retrieving data of patients with specific conditions usually limits size of a cohort and hampers analysis. EHR data exhibit many challenges such as heterogenous, longitudinally irregular, noisy, and incomplete nature of such data. It has been reported that more than 80% of efforts account for data collection and preparation. It is a challenge to represent data in a way that utilizes semantic relationship among medical concepts such that it can be easily integrated into further analytics. Thus, embodiments herein propose system 100 to generate specialized embedding for phenotypes comprised of a hybrid knowledge and data driven approach to expand data based on prior knowledge and generate specialized embedding using the hierarchical knowledge graph 109 for a selected cohort. Also, the embedded framework by data representation model, e.g., structural pheno-embedding model 108, that is fully trained on vendor data is exposed and it can be used by a client to generate embedding for the client's data. The model 108 that is initially trained on vendor's data can also be further tuned on the client's data for existing and new nodes. The model 108, if not trained on the vendor's data, can be fully trained on the client's data.

Figure 2:
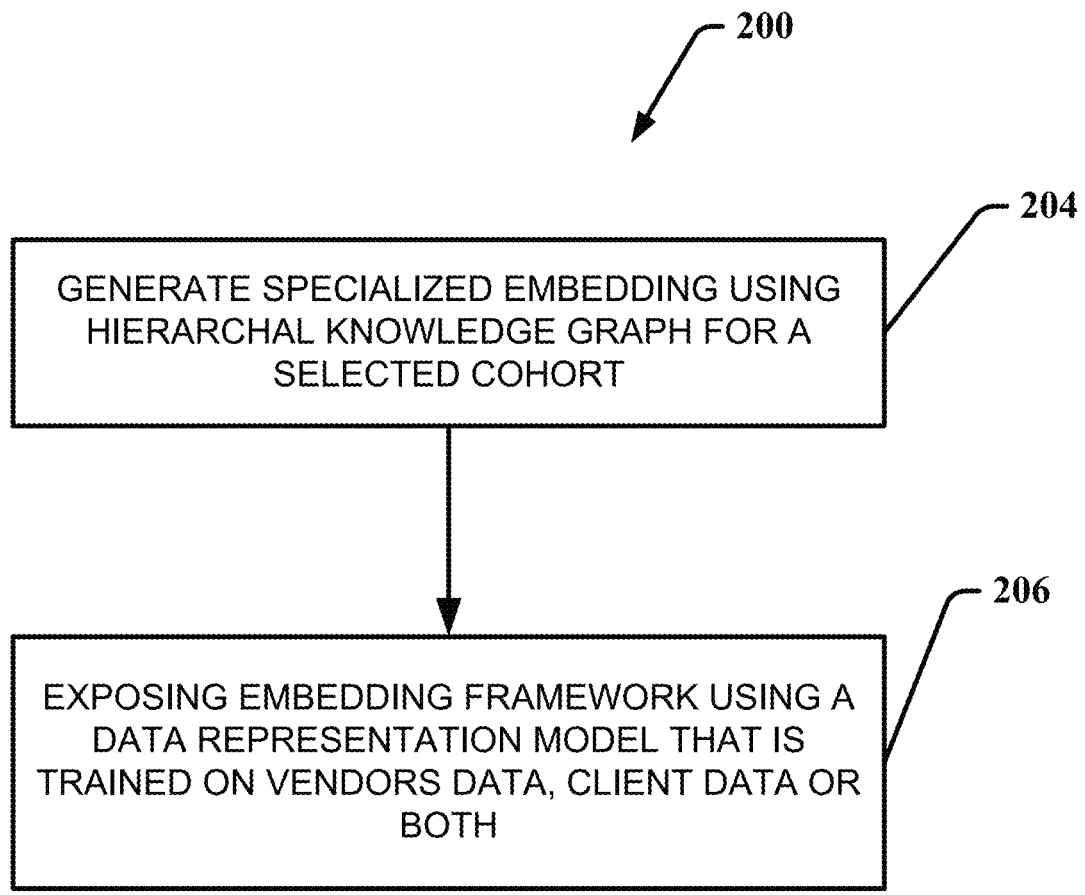
FIG. 2 illustrates an example flowchart of an integrated system to generate specialized embedding for phenotypes.

FIG. 2 illustrates an example framework 200 of a methodology to generate specialized embedding for phenotypes. Facets of the framework are data augmentation, representation of data, and a model to retrain the data. Two major problems for clients interested in a defined study for analytical models are data limitation and relevance of the data representation. A vendor owns and sells data to a client based on a criterion the client defines. It has been reported that more than 80% of efforts account for data collection and preparation. Thus, it is a challenge to represent the data that utilizes the semantic relationship among medical concepts such that it can be easily integrated into further analytics. Thus, the framework provides for a hybrid knowledge and data-driven approach that can expand data based on prior knowledge. In this way, data augmentation is performed with sparse data set and the enriched data can benefit the analytics. At 204, the framework generates specialized embedding using a hierarchical knowledge graph for a selected cohort. Thus, the patient's data is represented efficiently. Lastly, at 206, a model is used to expose the embedding framework in a data representation model. To generate a valuable representation for AI analysis, embodiments propose a data representation model 108 that generates a representation of patients that handles a specific disease as mentioned above. The model 108 has many parameters that need to be learned which can be performed based on vendor data, client data or a hybrid version where the model 108 initializes on the vendor data and adapts to client data. Through these embodiments, limitations on cohort selection, data enrichment (augmentation), and small data representation (embedding) can be resolved. Novelty of some embodiments is structured in two parts: representation learning of each phenotype is decoupled from prediction of outcome of interest to allow sharing of representations for patients with same phenotype for different predictive tasks; and secondly, ontology on network architecture is employed to share information among different but related phenotypes.

The specialized embedding for phenotypes can be examined in three different scenarios. The first scenario focuses on a model embedding when a client has no data. In this scenario, an input consists of cohort criteria that define a study for cohort expansion using vendor data. Also, a medical concept of ontology such as for example SNOMED CT can be used as a second input. Ontology relates medical concepts to one another. For example, a client might be interested in Type 2 Diabetes this would be used as the input. Type 1 Diabetes is a child of Diabetes and Type 2 Diabetes is a child of Diabetes. Thus, Type 1 and Type 2 diabetes are siblings of one another and this relationship is a known as a type of Ontology. In this case, SNOMED CT ontology is used wherein a node can represent one particular diagnosis code or a medical concept. In operation, a graph can be generated representing these medical concepts using the provided ontology. An interactive tool is used to select the vendor's data based on the client's specified criteria. If an initial code is given, ontology can be used to find other patients who have similar data as the initial code. An output of this step provides augmented data wherein an initial code is obtained from the client or the vendor and the system 100 is used to find similar information and then the data is augmented. The structural pheno-embedding model 108 is constructed using a knowledge graph 109 that is generated earlier. As the data is sparse, the ontology graph, e.g., hierarchical knowledge graph 109, is used to generate a useful representation of the patient's data. The vendor's data is selected based on the client's specified criteria and the constructed structural pheno-embedding model 108 is trained using the generated data. Upon training the model 108, the system 100 has three outcomes. Raw vendor's data is augmented based on the ontology, embeddings for the selected vendor's data is produced, and pheno-embeddings framework model is generated which can be used anywhere else in the architecture. Through the ontology graph 109, data that has a high affinity to sparse data can be found such that the sparse data can be made useful to construct any specific model.

In the proposed hierarchical multi-task approach, the model 108 decouples outcome nodes from phenotypical nodes. Input of phenotypical nodes are controlled by two gating mechanisms namely one to weight inputs from phenotypical parents and the other to control the input from shared representation. Each core node is associated with different outcome nodes and the output of the outcome node is a final prediction. For example, let $X=\{x_i \in R^d; \forall i\}$ be a matrix where $x_i$ represents a feature vector for record i with dimension d (e.g. vital signs and lab tests collected at the time of admission to the intensive care unit (ICU)). For each record i, the presence of all phenotypical medical concepts tied to i is assumed, as it is commonly done in EHR systems. For example, all diagnoses the patient developed are known at time of admission. This information is used to construct a subgraph G of an ontology with only nodes corresponding to medical concepts that are present in X. Any outcome prediction can be formulated as a mapping from X into an outcome set Y. To enable sharing across outcomes, the mapping is formed by defining an encoding function E: $X \rightarrow Z$, where Z is the representation space. For this representation, an unsupervised reconstruction process is incorporated by learning a reconstruction function R: Z→X. The generated representation can be used as an input to a standard supervised machine learning algorithm f to predict Y, f: Z→Y. Learning the parameters for the mappings E, R and f can be achieved by minimizing L:

$$L = \sum_i l(f(E(x_i)), y_i)_{-L_1} + \lambda \sum_i \|R(E(x_i)) - x_i\|_{2-L_2}$$

where $L_1$ is the total outcome prediction loss that aggregates the losses l (e.g. cross entropy for classification and mean square error for regression) at the node levels corresponding to the potentially different outcomes. $L_2$ is the reconstruction loss function. $\lambda \in R^+$ is a hyper-parameter that weighs the importance of the two losses. Learning a representation and a predictive model for one task is relatively straightforward by optimizing the equation above. However, learning such representations for multiple patient cohorts with different phenotypical profiles and multiple predictive tasks simultaneously is a challenging problem. Thus, these embodiments formalize by first describing a multi-task learner to decouple the outcome prediction and phenotypical representation in order to facilitate the incorporation of the hierarchical ontological structure as the second part of the model to address the aforementioned challenges.

Figure 3:
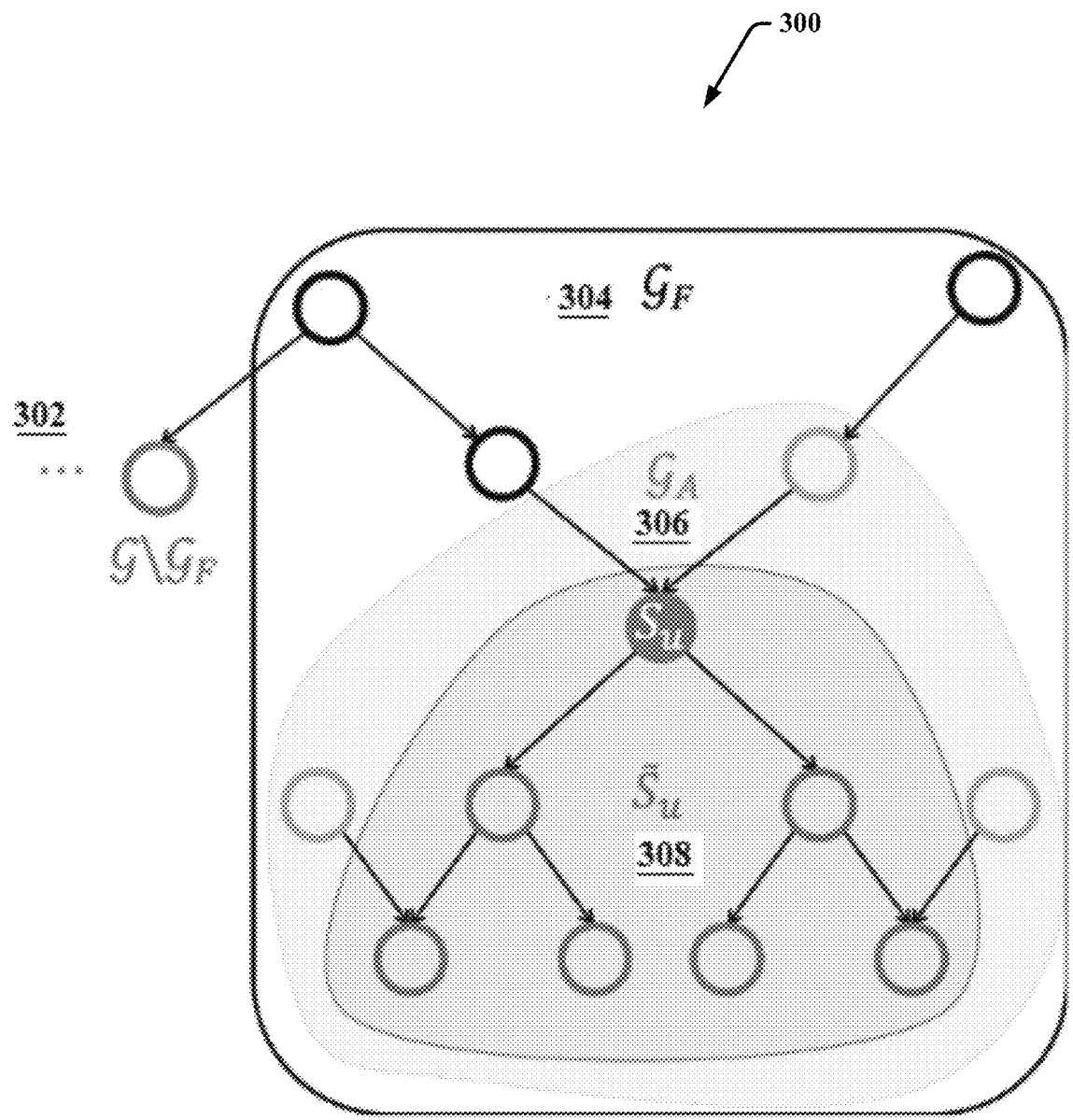
FIG. 3 illustrates an example architecture of data augmentation.

FIG. 3 illustrates an example architecture for data augmentation. As shown at knowledge graph 300, an input is a choice of medical concepts ontology such as SNOMED CT, a list of codes that define a concept of interest, a list of phenotypes of interest and minimum number of visits by nodes and minimum number of visits by the phenotypes of interest that a node can have. In an operation, graph G 302 is populated with number of visits at a node, and empirical distribution of phenotypes based on visits at this node. The graph 300 is filtered out at the nodes from G that are deemed not relevant such that filtered graph $G_F$ 304 has proximity to selected nodes. If a node in G has enough visits for analysis and if at least one of the phenotypes of interest is well represented in the visits, then the node is kept in G and its descendants are added to G else G is removed from the node. Thus, the collected nodes that are in the filtered graph $G_F$ 304 have proximity to the selected nodes, which is determined by the graph structure of $G_F$ 304, and are similar to the selected nodes by computing KL divergence between empirical distribution of phenotypes of candidate nodes and selected nodes. $G_A$ 306 graph are additional nodes that are added to the cohort and these nodes have proximity to nodes in 308. These datasets have similar characteristics to the initial cohort. A Monte Carlo sampling step is applied to decide how to sample nodes from candidate nodes. This entire procedure is applied recursively many times to grow graph nodes that are in direct proximity to an expanded set of nodes produced by a prior iteration. When similarity is measured, proximity from the knowledge graph is used to compare similarity based on final distribution. Output of this data augmentation is a filtered graph $G_A$ 304 along with the augmented data. Thus, in an implementation, in a populated graph G, initial nodes S are selected. A graph Gs is constructed with selected nodes and its descendants. Neighbours N in the graph Gs are selected and filtered based on similarity to Gs. Samples are obtained from filtered nodes, and selected nodes are augmented along with descendants. Upon augmenting the data, phenotypical embeddings are generated for a node in the filtered graph 300.

In phenotypical nodes, decoupling an outcome model is achieved wherein input data flows from a top into a mixture of expert nodes that are responsible for clustering an input subspace to facilitate representation computations. These expert nodes (E) can be denoted as:

$$E_e(\cdot), 1 \leq e \leq E$$

where each expert is a neural network producing a representation $E_e(x_i)$. Outputs of these expert nodes are consumed by an array of P phenotypical representation nodes denoted as:

$$P_p(\cdot), 1 \leq p \leq P$$

Each $P_p$ maps directly into one medical concept (e.g., the number of representation nodes is equal to the number of nodes in the subgraph G defined in FIG. 3 above). Each of these $P_p$ nodes ingest expert outputs via a gating function $G_p$ to learn how to combine information from expert nodes for generation of representations for a current medical concept. Gating network $G_p$ controls combination of expert nodes to produce input $M_p$ to representation node $P_p$. These are typically simple networks that produce combination weights for experts at each representation node:

$$G_p(x_i) = \text{Softmax}(x_i \cdot W_p + b_p) \in R^E M_p(x_i) = \sum_{e=1}^E G_p^e(x_i) E_e(x_i) \in$$

where $W_p \in R^E$, by E R are parameters to be learned by a gate network during training, and $G_p^e(x_i)$ is an entry e in vector $G_p(x_i)$. Input $M_p(x_i)$ is then passed to representation node $P_p$ to produce representations $E_p(x_i) = P_p(M_p(x_i))$ for current medical concept p. An objective of this part is to dynamically (using the gates) combine multiple experts for generation of useful representation for node p. Representations $E_p(.)$ are then passed as input to outcome nodes. The outcome nodes (stripped rectangle nodes) leverage representations to predict outcomes. Each outcome node can be modeled as a neural network with an objective of predicting outcome of interest. It is relevant to note that the framework can be optimized for multiple outcomes of interest as each representation node can have different and multiple outcomes, e.g., it can associate mortality prediction for certain medical concepts and readmission prediction for another (possibly overlapping) subset of medical concepts. This mimics the diabetic patients in our motivating example with two prediction tasks mortality and readmission.

Figure 4:
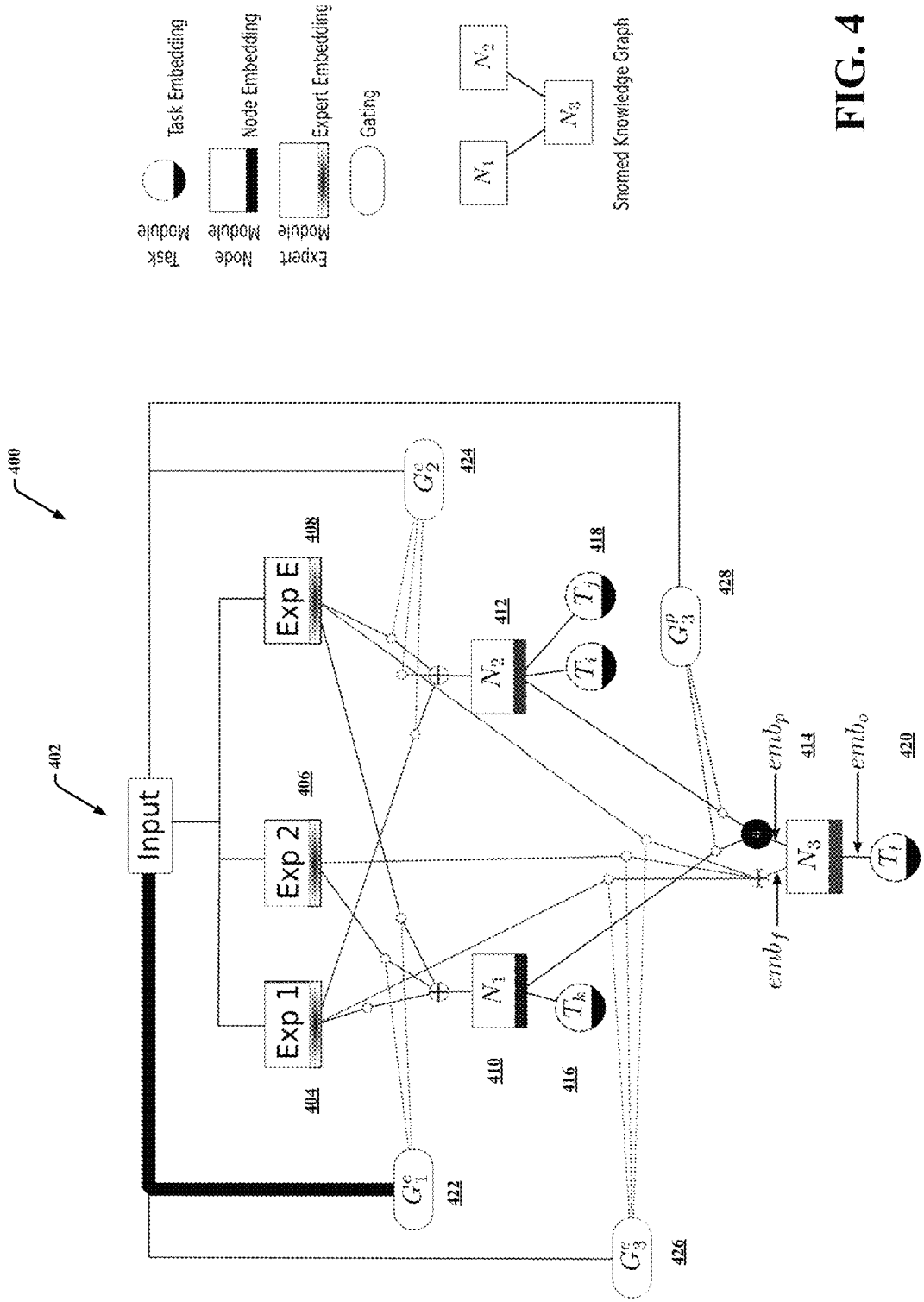
FIG. 4 illustrates an example architecture of phenotypical embedding generation of a node in the filtered graph.

FIG. 4 illustrates an example architecture of phenotypical embedding generation of a node in a filtered graph using augmented data. As illustrated at 400, a filtered graph from the data augmentation procedure and the augmented data populated in the filtered graph is used as input 402. In an operation, a model is created with multiple layers namely, experts, embedding components, expert gates, parent gates, and task components. A list of experts Exp 1 404, Exp 2 406, and Exp E 408 are used where experts take original data as an input. The experts could be thought of as a subspace of input space wherein an expert is a different way to look at a patient. A next layer has a list of embedding components $N_1$ 410, $N_2$ 412, and $N_3$ 414, wherein a component corresponds to a node in the filtered graph. Structure of the model follows the structure of the filtered graph. A component is responsible for generating an embedding for records that have the diagnosis code represented by the node. In the first layer, a representation of patient from different angels is generated and in the second layer, embeddings for one particular medical concept is generated and embeddings can be combined differently. The node $N_3$ 414 is not just looking at the representation from experts Exp 1 404, Exp 2 406, and Exp E 408 but is also looking at representation from nodes $N_1$ 410 and $N_2$ 412 as $N_3$ 414 is the child of $N_1$ and $N_2$. The model has a list of expert gates $G_1$ 422, $G_2$ 424, and $G_3$ 426 wherein a gate is responsible for determining how much experts contribute to embedding components. The model also has a list of parent gates $G_3^P$ 428 wherein a gate is responsible to determine how much a parent contributes to its child embedding component. The gates function can determine how to combine experts uniquely for a patient. The model has a list of task components 416, 418, and 420 wherein embeddings for different phenotypes can be further specialized to different tasks (e.g., predicting readmission or mortality). The task can check or predict if a patient with a particular disease is receptive to develop any other type of disease in the future. Moreover, when embedding is generated, that embedding could be general or specific to one particular task or multiple tasks. Thus, this representation is useful to predict mortality, re-admissions, or development of any other complications in the future. The model is trained to minimize a hierarchical loss function that has both reconstruction loss and task-specific loss that respects the hierarchical structure of the filtered graph. The output is a model that is trained to generate embeddings for a node in the filtered graph using the augmented data.

Depending on choice of phenotypes of interest, there can be a significant variation in the number of patients spanned by the representation nodes. For example, nodes corresponding to a higher-level concept (closer to the root) will typically span a much greater number of patients than the ones spanned by concepts at a leaf level of the ontology where concepts are very specialized. Interestingly, such nodes are semantically related via the medical concept ontology. Therefore, the generated representations across different medical concepts should share similar semantic relationships. Thus, these embodiments aim to increase the information sharing among these nodes using the ontology. The representation nodes are now connected by mirroring the ontology subgraph G. The representation nodes without ancestors can be computed using the same gating principle described in the sections above. However, for a node with ancestors, the model shares both the representation from the expert nodes and its parents. Assuming that $P_j$ has n parents, the resultant representation $E_j$ at $P_j$ is an aggregation of two vectors: (i) $M_j$ computed using the combination of experts and (ii) $P_j$ computed using the combination of the representations from the parents can be denoted by:

$$H_j(x_i) = \text{Softmax}(x_i \cdot W_j + b_j) P_j(x_i) = \Sigma_{k=1}^n H_j^k(x_i) E_k(x_i)$$

wherein the input to the node $P_j$ will be the aggregation of $M_j$ and $P_j$. The outcomes $E_j(x_i)$ can be computed as:

$$E_j(x_i) = P_j(M_j(x_i), P_j(x_i))$$

Using this strategy, ancestors of a representation node will be less affected by a 'vanishing data' problem and the structure thereby acts as a forcing mechanism to help the network learn the representation nodes and outcome with higher efficacy.

Figure 5:
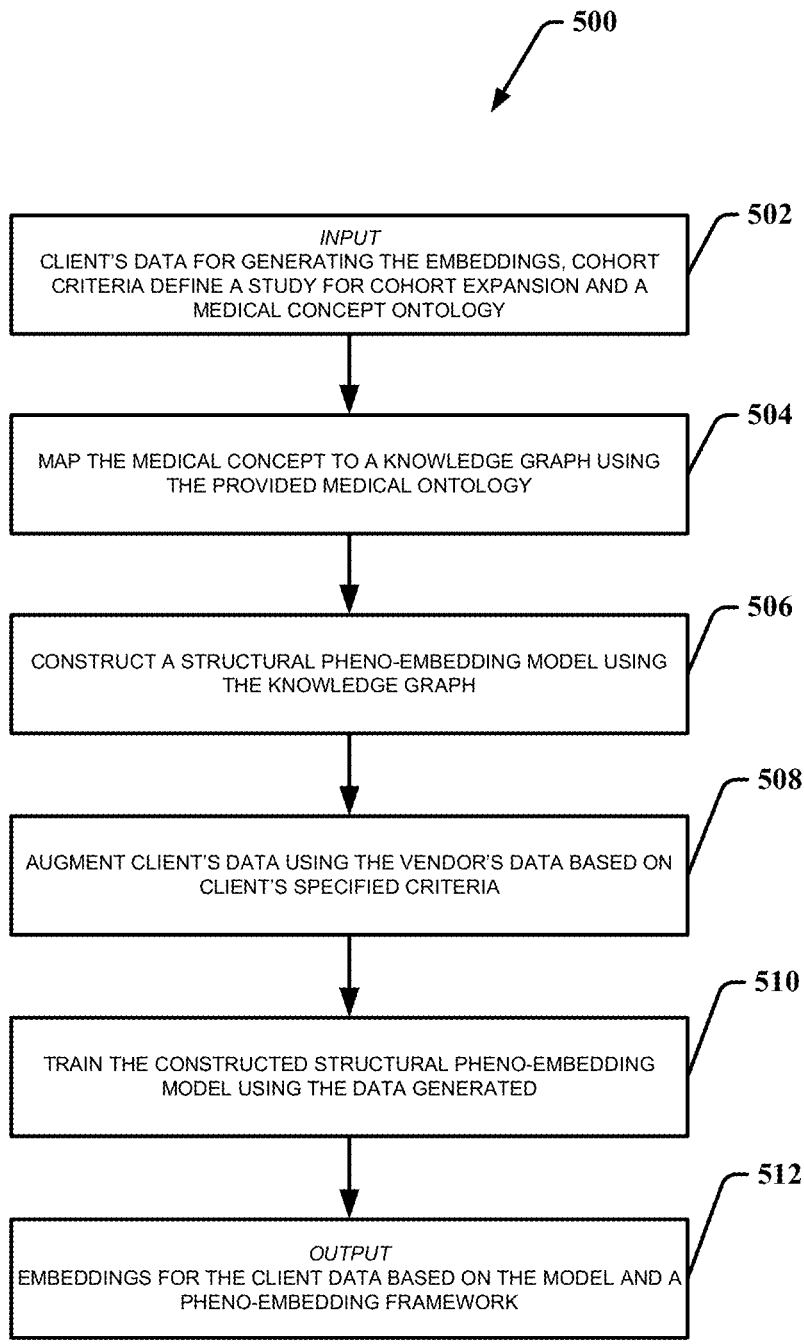
FIG. 5 illustrates an example flowchart of the system with client data and no vendor data.

FIG. 5 illustrates an example flowchart of the system with client data and no vendor data. As illustrated in 500, the input consists of the client's data that is used to generate the embeddings 502 along with cohort criteria that define a study for cohort expansion using the vendor's data and a choice of medical concept ontology. In an operation, the medical concepts are mapped to the knowledge graph using the provided medical ontology at 504. Using the interactive tool, the client's data is selected based on client's specified criteria. A structural pheno-embedding model is constructed at 506 using the knowledge graph generated at 502. The client's data is augmented using the vendor's data based on the client's specified criteria at 508. Then the structural pheno-embedding model is constructed at 506 and is trained at 510 using the data generated at 508. At 512 an output of this model has embeddings for the client data based on the model and a pheno-embedding framework. Thus, the model is trained using client data.

Figure 6:
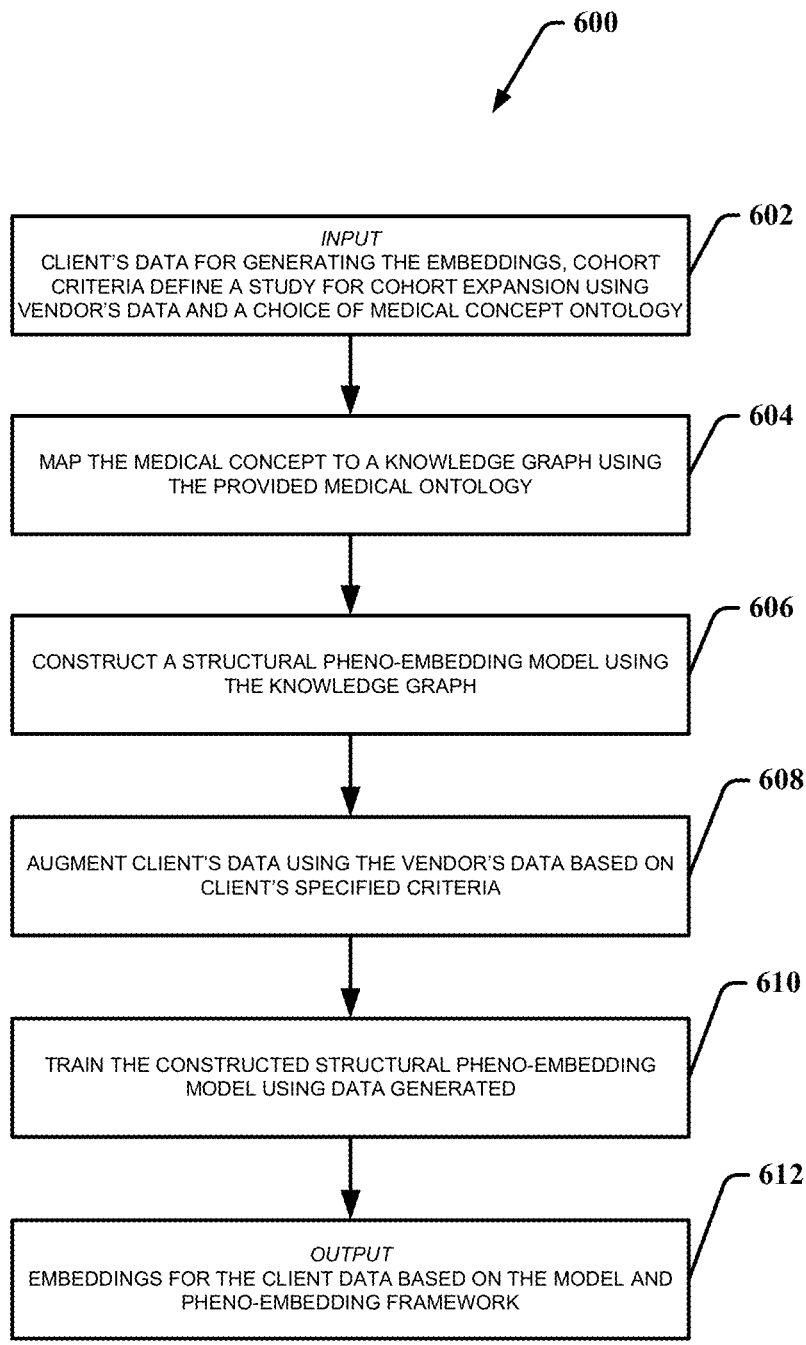
FIG. 6 illustrates an example flowchart of the system with client data and vendor data.

FIG. 6 illustrates an example flowchart of the system with client data and vendor data. As illustrated at 600, the input 602 consists of the client and the vendor's data along with the client's data for generating the embeddings, Cohort criteria that define a study for cohort expansion using vendor's data and a choice of medical concept ontology. In an operation, the medical concepts are mapped to a knowledge graph using the provided medical ontology at 604. A structural pheno-embedding model is constructed at 606 using the knowledge graph generated at 604. Then the client's data is augmented using vendor's data at 608 based on the client's specified criteria wherein both data are integrated using existing tools. A pheno-embedding model is constructed using the knowledge graph generated at 604. The constructed structural pheno-embedding model is trained at 610 using the data generated at 608. At 612, and output has embeddings for the client data based on the model and the output also has a pheno-embedding framework generated. Thus, in this scenario, the model is trained by using both client and vendor data.

Novelty of some embodiments is to generate pheno-embeddings that are specialized representations learned from different patient phenotypes addressing the data limitation and the lack of relevance of the embedding's issues. Conventional techniques use medical ontology towards more robust patient embeddings by imposing a multi-level hierarchy on EHR data defined by an ontology. The levels include visits, diagnosis, and treatments. While the proposed system tackles the data scarcity problem by using medical ontologies, it differs from work in intended use case(s) for using the ontologies to represent patients. Also, in another conventional technique, patient representations are learned as a weighted combination of the medical concepts in the ontology. Robust patient embeddings are attained by considering the hierarchy of medical events. While the proposed system is aimed at learning the patient representations for multiple phenotypes in a joint multi-task manner e.g. the same patient can have different representations depending on the phenotype of interest but still benefit from the information presented in more abundant phenotypes. Thus, embodiments learn such phenotypical patient representations using a novel system that multi-task and transfer learning with sparse gating mechanisms and domain knowledge to generate pheno-embeddings in a scalable manner.

Figure 7:
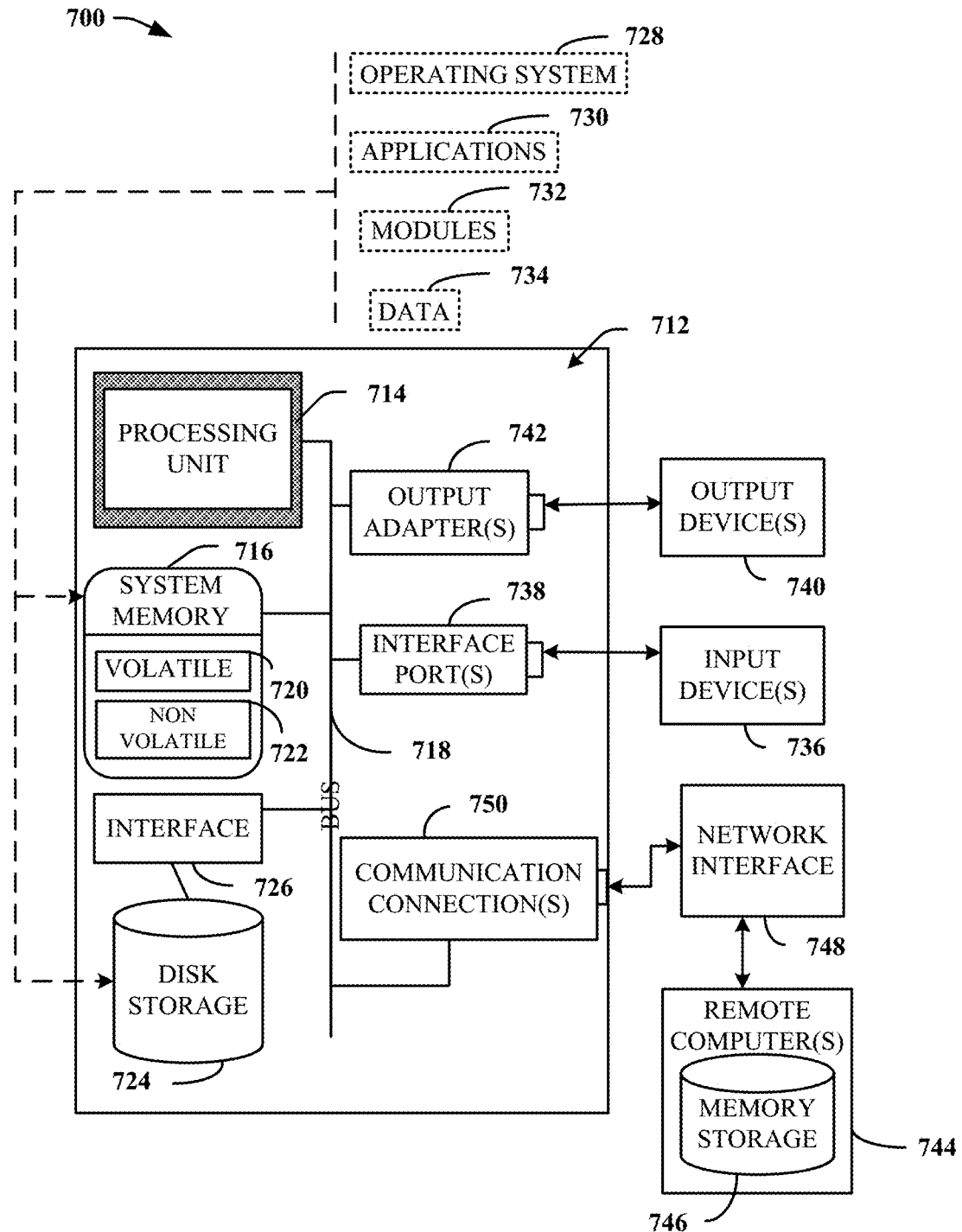
FIG. 7 illustrates a block diagram of an example, non-limiting, operating environment in which one or more embodiments described herein can be facilitated.

To provide a context for the various aspects of the disclosed subject matter, FIG. 7 as well as the following discussion are intended to provide a general description of a suitable environment in which the various aspects of the disclosed subject matter can be implemented. FIG. 7 illustrates a block diagram of an example, non-limiting operating environment in which one or more embodiments described herein can be facilitated. Repetitive description of like elements employed in other embodiments described herein is omitted for sake of brevity.

With reference to FIG. 7, a suitable operating environment 700 for implementing various aspects of this disclosure can also include a computer 712. The computer 712 can also include a processing unit 714, a system memory 716, and a system bus 718. The system bus 718 couples system components including, but not limited to, the system memory 716 to the processing unit 714. The processing unit 714 can be any of various available processors. Dual microprocessors and other multiprocessor architectures also can be employed as the processing unit 714. The system bus 718 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI).

The system memory 716 can also include volatile memory 720 and non-volatile memory 722. The basic input/output system (BIOS), containing the basic routines to transfer information between elements within the computer 712, such as during start-up, is stored in non-volatile memory 722. Computer 712 can also include removable/non-removable, volatile/non-volatile computer storage media. FIG. 7 illustrates, for example, a disk storage 724. Disk storage 724 can also include, but is not limited to, devices like a magnetic disk drive, floppy disk drive, tape drive, Jaz drive, Zip drive, LS-100 drive, flash memory card, or memory stick. The disk storage 724 also can include storage media separately or in combination with other storage media. To facilitate connection of the disk storage 724 to the system bus 718, a removable or non-removable interface is typically used, such as interface 726. FIG. 7 also depicts software that acts as an intermediary between users and the basic computer resources described in the suitable operating environment 700. Such software can also include, for example, an operating system 728. Operating system 728, which can be stored on disk storage 724, acts to control and allocate resources of the computer 712.

System applications 730 take advantage of the management of resources by operating system 728 through program modules 732 and program data 734, e.g., stored either in system memory 716 or on disk storage 724. It is to be appreciated that this disclosure can be implemented with various operating systems or combinations of operating systems. A user enters commands or information into the computer 712 through input device(s) 736. Input devices 736 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 714 through the system bus 718 via interface port(s) 738. Interface port(s) 738 include, for example, a serial port, a parallel port, a game port, and a universal serial bus (USB). Output device(s) 740 use some of the same type of ports as input device(s) 736. Thus, for example, a USB port can be used to provide input to computer 712, and to output information from computer 712 to an output device 740. Output adapter 742 is provided to illustrate that there are some output devices 740 like monitors, speakers, and printers, among other output devices 740, which require special adapters. The output adapters 742 include, by way of illustration and not limitation, video and sound cards that provide a means of connection between the output device 740 and the system bus 718. It is to be noted that other devices and/or systems of devices provide both input and output capabilities such as remote computer(s) 744.

Computer 712 can operate in a networked environment using logical connections to one or more remote computers, such as remote computer(s) 744. The remote computer(s) 744 can be a computer, a server, a router, a network PC, a workstation, a microprocessor based appliance, a peer device or other common network node and the like, and typically can also include many or all of the elements described relative to computer 712. For purposes of brevity, only a memory storage device 746 is illustrated with remote computer(s) 744. Remote computer(s) 744 is logically connected to computer 712 through a network interface 748 and then physically connected via communication connection 750. Network interface 748 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 750 refers to the hardware/software employed to connect the network interface 748 to the system bus 718. While communication connection 750 is shown for illustrative clarity inside computer 712, it can also be external to computer 712. The hardware/software for connection to the network interface 748 can also include, for exemplary purposes only, internal and external technologies such as, modems including regular telephone grade modems, cable modems and DSL modems, ISDN adapters, and Ethernet cards.

Figure 8:
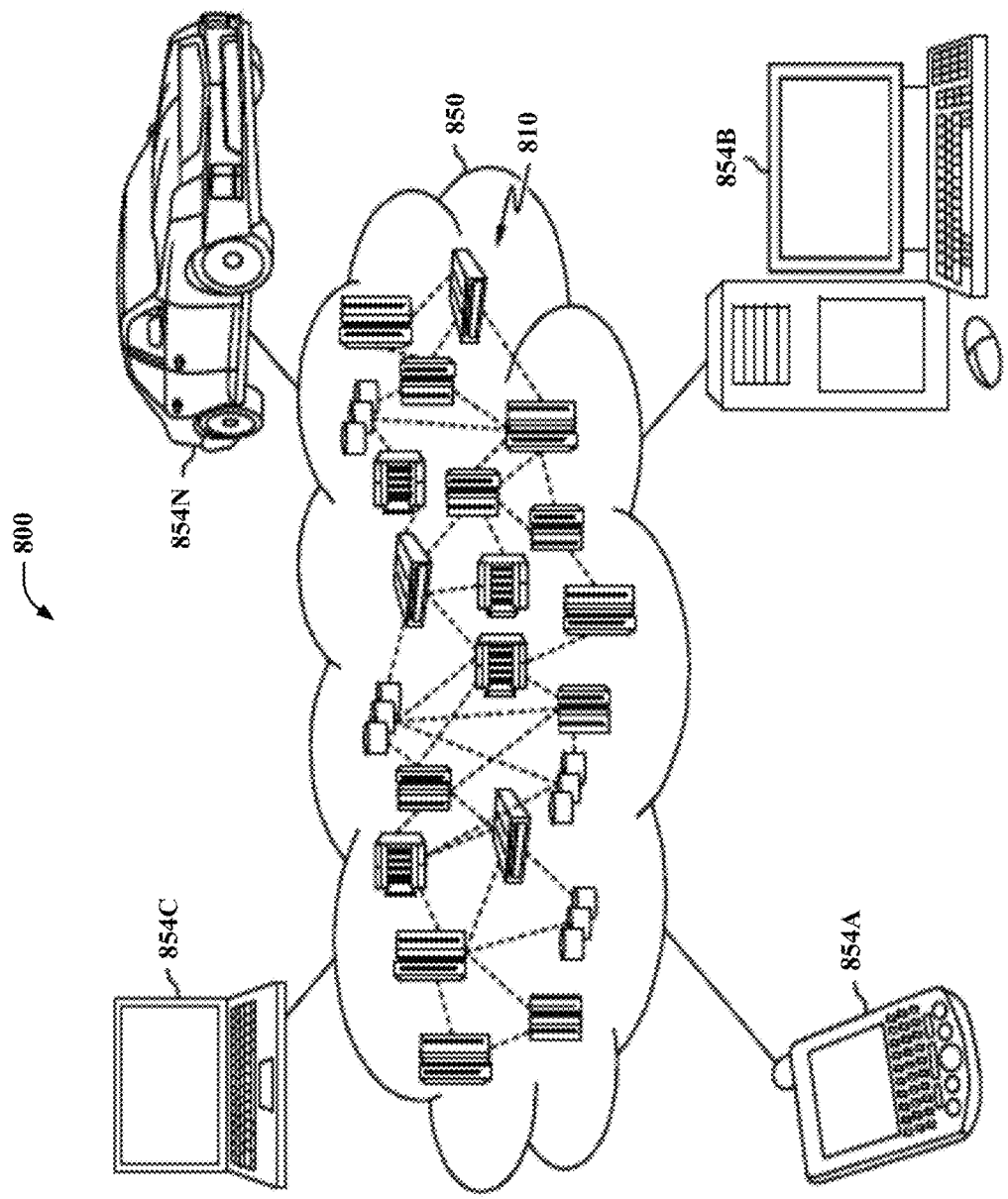
FIG. 8 illustrates a block diagram of an example, non-limiting, cloud computing environment in accordance with one or more embodiments of the subject disclosure.

Referring now to FIG. 8, an illustrative cloud computing environment 850 is depicted. As shown, cloud computing environment 850 includes one or more cloud computing nodes 810 with which local computing devices used by cloud consumers, such as, for example, personal digital assistant (PDA) or cellular telephone 854A, desktop computer 854B, laptop computer 854C, and/or automobile computer system 854N may communicate. Although not illustrated in FIG. 8, cloud computing nodes 810 can further comprise a quantum platform (e.g., quantum computer, quantum hardware, quantum software, etc.) with which local computing devices used by cloud consumers can communicate. Nodes 810 may communicate with one another. It may be grouped (not shown) physically or virtually, in one or more networks, such as Private, Community, Public, or Hybrid clouds as described hereinabove, or a combination thereof. This allows cloud computing environment 850 to offer infrastructure, platforms and/or software as services for which a cloud consumer does not need to maintain resources on a local computing device. It is understood that the types of computing devices 854A-N shown in FIG. 8 are intended to be illustrative only and that computing nodes 810 and cloud computing environment 850 can communicate with any type of computerized device over any type of network and/or network addressable connection (e.g., using a web browser).

Figure 9:
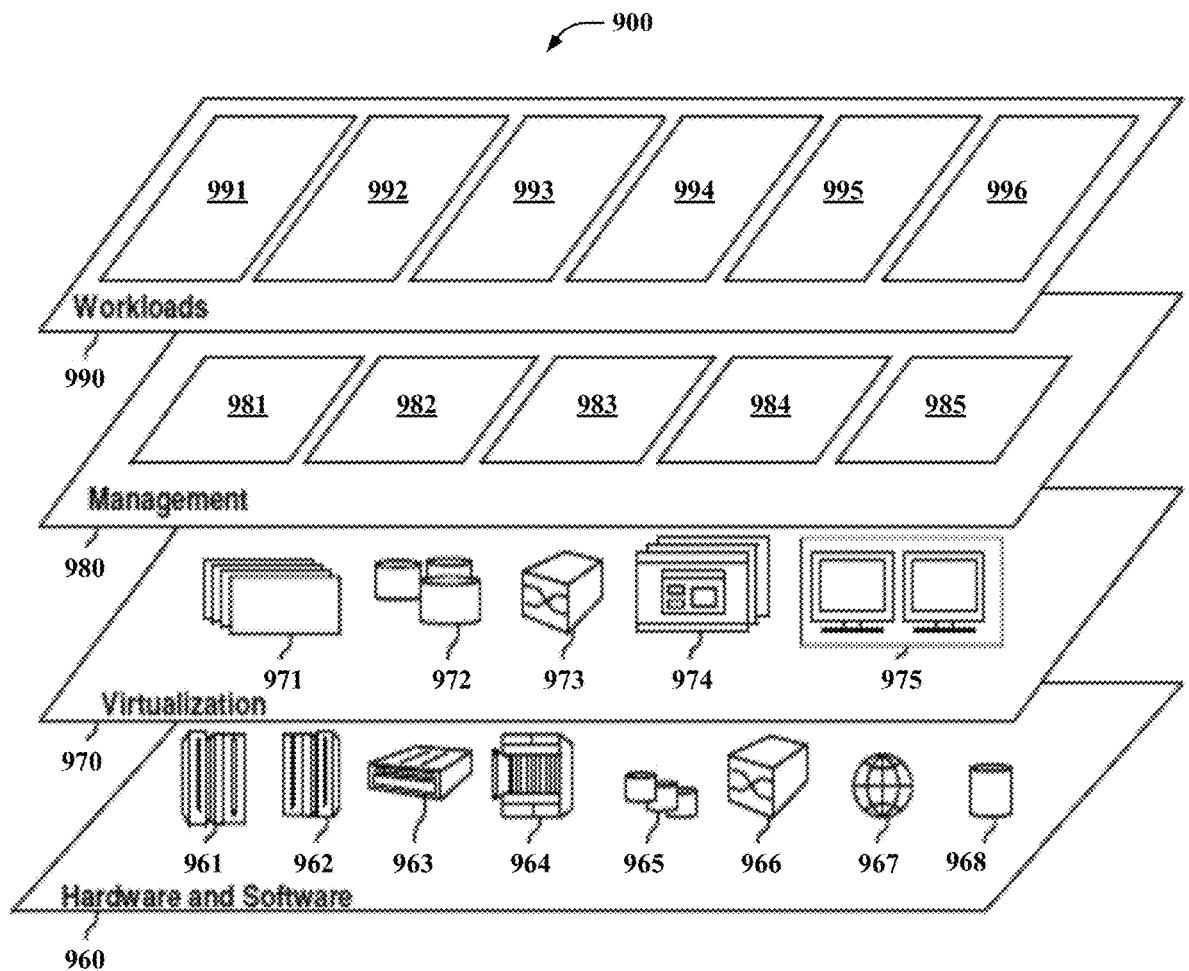
FIG. 9 illustrates a block diagram of example, non-limiting, abstraction model layers in accordance with one or more embodiments of the subject disclosure.

Referring now to FIG. 9, a set of functional abstraction layers provided by cloud computing environment 850 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 960 include hardware and software components. Examples of hardware components include mainframes 961; RISC (Reduced Instruction Set Computer) architecture-based servers 962; servers 963; blade servers 964; storage devices 965; and networks and networking components 966. In some embodiments, software components include network application server software 967, quantum platform routing software 968, and/or quantum software (not illustrated in FIG. 9).

Virtualization layer 970 provides an abstraction layer from which the following examples of virtual entities may be provided: virtual servers 971; virtual storage 972; virtual networks 973, including virtual private networks; virtual applications and operating systems 974; and virtual clients 975.

In one example, management layer 980 may provide the functions described below. Resource provisioning 981 provides dynamic procurement of computing resources and other resources that are utilized to perform tasks within the cloud computing environment. Metering and Pricing 982 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 983 provides access to the cloud computing environment for consumers and system administrators. Service level management 984 provides cloud computing resource allocation and management such that required service levels are met. Service Level Agreement (SLA) planning and fulfillment 985 provide pre-arrangement for, and procurement of, cloud computing resources for which a future requirement is anticipated in accordance with an SLA.

Workloads layer 990 provides examples of functionality for which the cloud computing environment may be utilized. Non-limiting examples of workloads and functions which may be provided from this layer include: mapping and navigation 991; software development and lifecycle management 992; virtual classroom education delivery 993; data analytics processing 994; transaction processing 995; and quantum state preparation software 996.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that the block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, the block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It can also be noted that the block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer (and/or computers), those skilled in the art can recognize that this disclosure also can or can be implemented in combination with other program modules. Generally, program modules include routines, programs, components, data structures, etc. that perform particular tasks and/or implement particular abstract data types. Moreover, those skilled in the art can appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or non-volatile memory, or can include both volatile and non-volatile memory. By way of illustration, and not limitation, non-volatile memory can include read only memory (ROM), programmable ROM (PROM), electrically programmable ROM (EPROM), electrically erasable ROM (EEPROM), flash memory, or non-volatile random-access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory that stores computer executable components; and
a processor that executes the computer executable components stored in memory, wherein the computer executable components comprise:
a training component that trains a structural pheno-embedding learning model, using a hierarchical knowledge graph of phenotypes and a set of patient data mapped to the hierarchical knowledge graph, to perform cohort expansion based on relationships of the phenotypes of the hierarchical knowledge graph;
a data augmentation component that expands, using the structural pheno-embedding learning model and the hierarchical knowledge graph, a sparse data set of client's patient data of a selected cohort based on a client's cohort selection criteria comprising a phenotype to generate an augmented data set comprising an expanded cohort using a subset of the set of patient data; and
an embedding component that generates, using the structural pheno-embedding learning model and the augmented data set, a filtered graph from the hierarchical knowledge graph, wherein the filtered graph comprises specialized embeddings for a subset of the phenotypes of the hierarchical knowledge graph associated with the phenotype.

2. The system of claim 1, further comprising a graph generation component that populates the hierarchical knowledge graph from an ontology of phenotypes.

3. The system of claim 1, further comprising a model generation component that generates the structural pheno-embedding learning model using the hierarchical knowledge graph.

4. The system of claim 1, wherein the set of patient data comprises a set of vendor patient data.

5. The system of claim 1, wherein the structural pheno-embedding learning model comprises layers selected from a group of layers comprising a layer of expert nodes, a layer of embedding components, a layer of expert gates, a layer of parent gates, and a layer of task components.

6. The system of claim 1, wherein the structural pheno-embedding learning model is further trained to learn patient representations for multiple phonotypes in a joint multi-task manner.

7. The system of claim 1, wherein the structural pheno-embedding learning model is further trained to minimize a hierarchical loss function that comprises reconstruction loss and task-specific loss.

8. A computer-implemented method, comprising:
using training, by a system operatively coupled to a processor, a structural pheno-embedding model, using a hierarchical knowledge graph of phenotypes and a set of patient data mapped to the hierarchical knowledge graph, to perform cohort expansion based on relationships of the phenotypes of the hierarchical knowledge graph;
expanding, by the system, using the structural pheno-embedding learning model and the hierarchical knowledge graph, a sparse set of client's patient data of a selected cohort based on a client's cohort selection criteria comprising a phenotype to generate an augmented data set comprising an expanded cohort using a subset of the set of patient data; and
generating, by the system, using the structural pheno-embedding learning model and the augmented data set, a filtered graph from the hierarchical knowledge graph, wherein the filtered graph comprises specialized embeddings for a subset of the phenotypes of the hierarchical knowledge graph associated with the phenotype.

9. The computer-implemented method of claim 8, further comprises populating, by the system, the hierarchical knowledge graph from an ontology of phenotypes.

10. The computer-implemented method of claim 8, further comprising generating, by the system, the structural pheno-embedding learning model using the hierarchical knowledge graph.

11. The computer-implemented method of claim 8, wherein the set of patient data comprises a set of vendor patient data.

12. The computer-implemented method of claim 8, wherein the structural pheno-embedding learning model comprises layers selected from a group of layers comprising a layer of expert nodes, a layer of embedding components, a layer of expert gates, a layer of parent gates, and a layer of task components.

13. The computer-implemented method of claim 8, wherein the structural pheno-embedding learning model is further trained to learn patient representations for multiple phonotypes in a joint multi-task manner.

14. The computer-implemented method of claim 8, wherein the structural pheno-embedding learning model is further trained to minimize a hierarchical loss function that comprises reconstruction loss and task-specific loss.

15. A computer program product comprising a computer readable storage medium having program instructions embodied therewith, the program instructions executable by a processor to cause the processor to:
    train a structural pheno-embedding learning model, using a hierarchical knowledge graph of phenotypes and a set of patient data mapped to the hierarchical knowledge graph, to perform cohort expansion based on relationships of the phenotypes of the hierarchical knowledge graph;
    expand, using the structural pheno-embedding learning model and the hierarchical knowledge graph, a sparse set of client's patient data of a selected cohort based on a client's cohort selection criteria comprising a phenotype to generate an augmented data set comprising an expanded cohort using a subset of the set of patient data; and
    generate, using the structural pheno-embedding learning model and the augmented data set, a filtered graph from the hierarchical knowledge graph, wherein the filtered graph comprises specialized embeddings for a subset of the phenotypes of the hierarchical knowledge graph associated with the phenotype.

16. The computer program product of claim 15, wherein the program instructions are further executable by the processor to further cause the processor to: populate the hierarchical knowledge graph from an ontology of phenotypes.

17. The computer program product of claim 15, wherein the program instructions are further executable by the processor to further cause the processor to: generate the structural pheno-embedding learning model using the hierarchical knowledge graph.

18. The computer program product of claim 15, wherein the set of patient data comprises a set of vendor patient data.

19. The computer program product of claim 15, wherein the structural pheno-embedding learning model comprises layers selected from a group of layers comprising a layer of expert nodes, a layer of embedding components, a layer of expert gates, a layer of parent gates, and a layer of task components.

20. The computer program product of claim 15, wherein the structural pheno-embedding learning model is further trained to learn patient representations for multiple phonotypes in a joint multi-task manner.

21. The computer program product of claim 15, wherein the structural pheno-embedding learning model is further trained to minimize a hierarchical loss function that comprises reconstruction loss and task-specific loss.

* * * * *